United States Patent [19]

Lipinski

[11] 4,276,297

[45] Jun. 30, 1981

[54] PYRIDYLAMINOTRIAZOLE THERAPEUTIC AGENTS

[75] Inventor: Christopher A. Lipinski, Waterford, Conn.

[73] Assignee: Pfizer Inc., New York, N.Y.

[21] Appl. No.: 49,737

[22] Filed: Jun. 18, 1979

[51] Int. Cl.³ ................... A61K 31/44; C07D 401/04
[52] U.S. Cl. .................................. 424/263; 546/276; 546/310; 546/324
[58] Field of Search ......................... 424/263; 546/276

[56] References Cited

U.S. PATENT DOCUMENTS

| | | | |
|---|---|---|---|
| 3,647,814 | 3/1972 | Greenfield | 546/276 |
| 3,663,527 | 5/1972 | Schonenbuch . | |
| 3,813,400 | 5/1974 | Boyle et al. | 546/276 |
| 3,873,563 | 3/1975 | Kotone et al. | 546/276 X |
| 3,879,404 | 4/1975 | Baldwin et al. | 546/276 |
| 4,071,518 | 1/1978 | Baldwin et al. | 546/276 |
| 4,102,889 | 7/1978 | Baldwin et al. | 546/276 |

FOREIGN PATENT DOCUMENTS 1925654 10/1969 Fed. Rep. of Germany .
1934551 1/1970 Fed. Rep. of Germany .

OTHER PUBLICATIONS

Chem. Abstracts 48:12092 d.
Chem. Abstracts 58:5703 h.
Annual Reports in Medicinal Chem., vol. 14, pp. 91–102, (1979).
Bieman et al., *Monatshefte fur Chemie*, vol. 89, Nos. 4–5, p. 603, (1958).
Jones et al., Journ. Medicinal Chem., vol. 8, p. 676, (1965).
Yakugaku Zashi, Journ. Pharm. Soc. Japan, vol. 92, No. 4, p. 471, (1972).

Primary Examiner—Ethel G. Love
Attorney, Agent, or Firm—Connolly and Hutz

[57] ABSTRACT

A series of novel 3-amino-5-(4-pyridyl)-1,2,4-triazole derivatives has been prepared, including their pharmaceutically acceptable acid addition salts. These particular compounds are useful in therapy as anti-ulcer agents. Preferred member compounds include 3-amino-5-[2-(N-monomethylamino)-4-pyridyl]-1,2,4-triazole, 3-amino-5-[2-(N-monoethylamino)-4-pyridyl]-1,2,4-triazole and 3-amino-5-[2-(N,N-dimethylamino)-4-pyridyl]-1,2,4-triazole. Alternate methods of preparation are provided and the principal synthetic routes leading to the preferred compounds are described in some detail.

25 Claims, No Drawings

PYRIDYLAMINOTRIAZOLE THERAPEUTIC AGENTS

BACKGROUND OF THE INVENTION

This invention relates to new and useful pyridylaminotriazole derivatives of principal interest to those in the field of medicinal chemistry and/or chemotherapy. More particularly, it is concerned with a novel series of 3-amino-5-(4-pyridyl)-1,2,4-triazole compounds, which are of especial value in view of their unique anti-ulcer properties. The invention also includes a new method of therapy within its scope.

In the past, various attempts have been made by numerous investigators in the field of organic medicinal chemistry to obtain new and better anti-ulcer agents. For the most part, these efforts have involved the synthesis and testing of various heretofore new and unavailable organic compounds, particularly in the area of organic heterocyclic bases, in an endeavor to determine their ability to inhibit the secretion of gastric acid in the stomach without causing any substantial anticholinergic side effects to occur that might possibly be considered undesirable from a pharmacological point of view. However, in the search for newer and still better or more improved anti-ulcer agents, far less is known about the effect (particularly on peptic ulcers) of other organic compounds in this area which could proceed in the body via a non-anticholinergic mechanism and yet still possess gastric acid antisecretory properties. Nevertheless, G. J. Durant et al., in U.S. Pat. Nos. 4,022,797, 4,024,271 and 4,027,026 do disclose that certain histamine $H_2$-receptor inhibitors in the thioalkyl-, aminoalkyl- and oxyalkylguanidine series and in the pyridyl-substituted thioalkyl- and oxyalkylthiourea series, respectively, are useful for these purposes even though these particular compounds are not known to be anticholinergic per se. These particular histamine $H_2$-receptor inhibitors all function by antagonizing those responses to histamine, such as the stimulation of the secretion of gastric acid in the stomach, which cannot be blocked by the action of a histamine $H_1$-receptor antagonist like mepyramine, for example. As a result, these compounds are definitely of value as histamine $H_2$-receptor inhibitors for controlling gastric acidity and are therefore useful in the treatment of peptic ulcers and other like conditions of the body, etc.

SUMMARY OF THE INVENTION

In accordance with the present invention, it has now been rather surprisingly found that various novel 3-amino-5-(4-pyridyl)-1,2,4-triazole derivatives are extremely useful when employed in therapy as histamine $H_2$-receptor inhibitors for the control of peptic ulcers and other conditions caused or exacerbated by gastric hyperacidity. More specifically, the novel compounds of this invention are all selected from the group consisting of 3-amino-5-(4-pyridyl)-1,2,4-triazole bases of the formula:

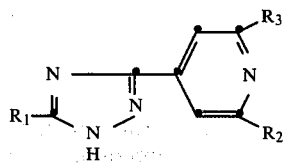

and the pharmaceutically acceptable acid addition salts thereof, wherein $R_1$ is a member selected from the group consisting of amino, lower N-monoalkylamino and lower N,N-dialkylamino; $R_2$ is a member selected from the group consisting of amino, N-monoalkylamino having from one to twelve carbon atoms, N,N-dialkylamino wherein at least one of said alkyl moieties is methyl or ethyl and the other is alkyl having from one to twelve carbon atoms, N-monoallylamino, N-monomethallylamino, N-methyl-N-allylamino, N-ethyl-N-allylamino, N-mono-($\beta$-hydroxyethyl)-amino, N-mono($\gamma$-hydroxypropyl)amino, N-mono[$\beta$-(lower alkoxy)ethyl]amino, N-mono[$\gamma$-(lower alkoxy)propyl]amino, N-mono(2,2,2-trifluoroethyl)-amino, N-monobenzylamino, N-methyl-N-benzylamino, N-ethyl-N-benzylamino, N-mono($\beta$-phenylethyl)amino, N-mono($\beta$-phenyl-$\beta$-hydroxyethyl)amino, and ring-substituted N-monobenzylamino, ring-substituted N-methyl-N-benzylamino, ring-substituted N-ethyl-N-benzylamino and ring-substituted N-mono($\beta$-phenylethyl)amino with each ring having up to two substituents on the phenyl moiety wherein each of said ring-substituents is identically chosen from the group consisting of fluorine, chlorine, bromine, trifluoromethyl, lower alkyl, lower alkoxy, hydroxy, carbamoyl, sulfamoyl, lower alkylsulfonyl and methanesulfonamido, or is separately chosen from the group consisting of chlorine, methyl, methoxy, hydroxy and trifluoromethyl; and $R_3$ is a member selected from the group consisting of hydrogen, lower alkyl, amino and lower N-monoalkylamino. These novel compounds all possess anti-ulcer activity to a statistically significant high degree, particularly in view of their ability to inhibit the secretion of gastric acid in the body and are therefore extremely useful in the treatment of peptic ulcers and other like conditions.

Of especial interest in this connection are such typical and preferred member compounds of the invention as 3-amino-5-[2-(N-monomethylamino)-4-pyridyl]-1,2,4-triazole, 3-amino-5-[2-(N-monoethylamino)-4-pyridyl]-1,2,4-triazole, 3-amino-5-[2-(N,N-dimethylamino)-4-pyridyl]-1,2,4-triazole, 3-amino-5-[2-(N-ethyl-N-methylamino)-4-pyridyl]-1,2,4-triazole and 3-amino-5-[2-(N,N-diethylamino)-4-pyridyl]-1,2,4-triazole, respectively. These particular compounds are all highly potent as regards their anti-ulcer activity, especially in view of their ability to inhibit gastric acid secretion in the body to a rather substantially high degree.

DETAILED DESCRIPTION OF THE INVENTION

In accordance with the principal process employed for preparing the novel compounds of this invention, an appropriately substituted 2-haloisonicotinic acid 2-amidinohydrazide of the formula:

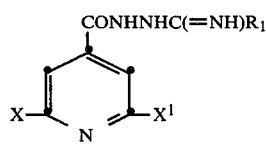

wherein X is either chlorine or bromine and $X^1$ is hydrogen, lower alkyl, chlorine or bromine, is condensed with an appropriate amine base of the corresponding formula $R_2H$, wherein $R_2$ is as previously defined, to yield the desired 3-amino-5-(4-pyridyl)-1,2,4-triazole final product having the same structural formula as previously indicated. This particular reaction is normally carried out by using an excess of the organic amine base with respect to the required mono- or dimolar reaction ratio, since this tends to shift the reaction equilibrium to the product side of the equation for the present purposes at hand. In addition, the excess amine can also function as a solvent for the reaction, with a preferred excess for these purposes being from about three to about ten moles of amine per one mole of halogen starting material. On the other hand, a reaction-inert organic solvent may also be used for the reaction and this would ordinarily entail employment of an aromatic hydrocarbon solvent such as benzene, toluene and xylene, or a cyclic ether such as dioxane and tetrahydrofuran, or a lower alkanol like methanol, ethanol or isoamyl alcohol, etc. In addition, the reaction can also be carried out in an aqueous solvent medium. The temperature at which the reaction can be conducted varies widely and generally falls within the temperature range of from about 80° C. up to about 250° C. for a period of about five to about 120 hours (i.e., until all the water of reaction has been substantially removed from the reaction mixture). A preferred reaction time and temperature for the process would be about 150°–200° C. for a period of approximately 12–72 hours. In the case where a particular solvent is used and/or the boiling point of the amine is below the desired reaction temperature range, it is often customary in practice to employ a sealed pressure vessel in which to conduct the reaction. Upon completion of this step, recovery of the desired product is then readily effected by a number of conventional means. For instance, the cooled reaction mixture is first concentrated in vacuo to remove the solvent and the product subsequently isolated by means of filtration or trituration with another organic solvent such as ethyl acetate or ethanol, followed by further purification (if necessary) via crystallization, recrystallization and column chromatography, etc. In this way, high yields of the pure pyridylaminotriazole final product are easily obtained. It should also be noted in this connection that the 2-halo and 2,6-dihaloisonicotinic acid 2-amidinohydrazide starting materials and the amines ($R_2H$) employed as reagent in this reaction are, for the most part, known compounds or else they are easily prepared by those skilled in the art from more readily available starting materials using the standard procedures of organic chemistry.

An alternate and equally facile route leading to the production of the novel 3-amino-5-(4-pyridyl)-1,2,4-triazole base compounds of this invention involves heating the corresponding 2-aminoisonicotinic acid 2-amidinohydrazide of the formula:

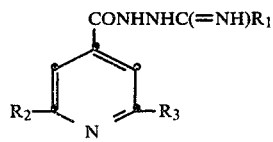

wherein $R_2$ and $R_3$ are each as previously defined, whereupon the desired ring-closure step conveniently takes place (via an internal condensation reaction) to afford a compound having the same aforesaid structural formula as previously defined for the desired final products of this invention. This particular condensation reaction is normally conducted in the absence of a solvent at a temperature that generally lies within the range of from about 150° C. up to about 300° C. for a period of about five minutes up to about 6–8 hours. The reaction may also be conducted in a sealed pressure vessel in the presence of a solvent such as an aromatic hydrocarbon solvent like benzene, toluene, xylene, etc., or any other reaction-inert organic solvent, such as a cyclic ether like tetrahydrofuran or dioxane. Upon completion of the reaction, the desired pyridylaminotriazole final product is easily isolated from the reaction mixture in a conventional manner, e.g., by cooling same to room temperature and then recrystallizing from a suitable solvent system such as ethyl acetate/methanol or even from pure water alone. As regards the 2-aminoisonicotinic acid 2-amidinohydrazides used as starting materials in the above reaction, these are either known compounds or else they are easily prepared by those skilled in the art starting from the corresponding 2-aminoisonicotinic acid hydrazides by reacting the latter type compounds with the appropriate 2-substituted-2-thiopseudourea of choice.

Still other methods which can be used for preparing the novel 3-amino-5-(4-pyridyl)-1,2,4-triazole compounds of this invention involve routes which do not proceed from the corresponding aforementioned 2-halo or 2-aminoisonicotinic acid 2-amidinohydrazide starting materials and these include the following, viz., (1) the fusion reaction of an appropriately substituted 2-aminoisonicotinic acid with an appropriate aminoguanidine salt, such as the sulfate, at elevated temperatures (e.g., 200°–220° C.); (2) the reaction of an appropriate 2-aminoisonicotinic acid hydrazide with the proper 2-substituted-2-thiopseudourea salt (e.g., a hydrohalide salt) in the presence of an aqueous base; and (3) the conversion of an appropriately substituted 3-amino-5-(2-halo or 2,6-dihalo-4-pyridyl)-1,2,4-triazole to the corresponding 3-amino-5-(2-amino or 2,6-diamino-4-pyridyl)-1,2,4-triazole final product by treatment with an appropriate amine at elevated temperatures (e.g., 150°–250° C.).

Of these three remaining alternate routes briefly discussed above, the most preferred one is the second method involving the reaction of an appropriately substituted 2-aminoisonicotinic acid hydrazide with a suitable 2-substituted-2-thiopseudourea salt in the presence of an aqueous base. This particular reaction is normally carried out in a suitable aqueous solvent medium at a temperature ranging from about 20° C. up to about 100° C. for a period of about two to about 100 hours. Suitable aqueous solvents for these purposes generally include reaction-inert polar solvents like water, as well as various mixtures thereof with cyclic ethers such as dioxane and tetrahydrofuran, etc. The base employed can be any inorganic or organic base that is soluble in the system and is preferably an alkali metal hydroxide such as lithium, sodium or potassium hydroxide. It must be present in sufficient amount to liberate the 2-substituted-2-thiopseudourea from its salt and is preferably present in an amount sufficient to maintain the pH of the resulting aqueous mixture in a range that is at least above about pH 8.0. Upon completion of the reaction, the desired product is easily recovered by any number of conventional means such as filtration of the reaction mixture or column chromatography of same, if absolutely necessary.

As regards the alternate route involving the condensation reaction of an appropriately substituted 2-aminoisonicotinic acid with an appropriate aminoguanidine salt, this step can be carried out in essentially the same manner as was previously described for the fusion reaction of the corresponding 2-aminoisonicotinic acid 2-amidinohydrazide (which subsequently led to the desired final product via an intenal condensation). In this particular case, the condensation/and ring-closure step is effected at a temperature that generally is in the range of from about 150° C. up to about 250° C. for a period of about one to about 20 hours. Isolation of the desired pyridylaminotriazole final product from the spent reaction mixture is then easily effected by taking advantage of the acidic nature of the 2-aminoisonicotinic acid starting material, as is more fully described in the experimental sections of the instant specification (see Examples XXII–XXIV and XXX).

As regards the alternate route involving the conversion of an appropriately substituted 3-amino-5-(2-halo or 2,6-dihalo-4-pyridyl)-1,2,4-triazole compound to the corresponding 3-amino-5-(2-amino or 2,6-diamino-4-pyridyl)-1,2,4-triazole via a metathetical reaction with the appropriate amine base, this step can be accomplished in essentially the same manner as was earlier described for the principal process method of this invention involving the reaction between an appropriately substituted 2-haloisonicotinic acid 2-amidinohydrazide and the same corresponding amine ($R_2H$). In this particular case, the starting halogen compounds is either a mono- or di-chlorine or bromine derivative and the final product is isolated in a rather conventional manner (e.g., by partitioning the reaction residue between two immiscible solvents or using thin layer chromatography, etc).

The pharmaceutically acceptable acid addition salts of the 3-amino-5-(4-pyridyl)-1,2,4-triazole base compounds of this invention are prepared by simply treating the aforementioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by simply using the proper molar amount of the appropriate acid in an aqueous solvent medium or in a suitable organic solvent such as methanol or ethanol. Upon careful evaporation of the solvent, the solid salt is readily obtained.

As previously indicated, the 3-amino-5-(4-pyridyl)-1,2,4-triazole compounds of this invention are all readily adapted to therapeutic use as histamine $H_2$-receptor inhibitors for the control of peptic ulcers, especially in view of their ability to inhibit the secretion of gastric acid in the body to a statistically significant degree. For instance, 3-amino-5-[2-(N-monoethylamino)-4-pyridyl]-1,2,4-triazole, a typical and preferred agent of the present invention, has been found to consistently inhibit the pentagastrin-induced secretion of gastric acid from stomachs of Heidenhain pouch dogs to a significantly high degree when given by the intravenous route of administration at dose levels ranging from 1.0 mg./kg. to 10 mg./kg., respectively, without showing any substantial signs of toxic side effects. The other compounds of this invention also cause similar results. Furthermore, all the herein described compounds of this invention can be administered orally, for the present purposes at hand, without causing any significant untoward pharmacological side reactions to occur in the subject to whom they are so administered. In general, these compounds are ordinarily administered at dosage levels ranging from about 0.5 mg. to about 50 mg. per kg. of body weight per day, although variations will necessarily occur depending upon the condition and individual response of the subject being treated and the particular type of pharmaceutical formulation chosen.

In connection with the use of the 3-amino-5-(4-pyridyl)-1,2,4-triazole compounds of this invention for the treatment of subjects afflicted with peptic ulcers, it is to be noted that they may be administered either alone or in combination with pharmaceutically acceptable carriers and that such administration can be carried out in both single and multiple dosages. More particularly, the novel compounds of this invention can be administered in a wide variety of different dosage forms, i.e., they may be combined with various pharmaceutically acceptable inert carriers in the form of tablets, capsules, lozenges, troches, hard candies, powders, aqueous suspensions, elixirs, syrups and the like. Such carriers include solid diluents or fillers, sterile aqueous media and various non-toxic organic solvents, etc. Moreover, such standard pharmaceutical compositions can be suitable sweetened and/or flavored by means of various agents of the type commonly employed for just such a purpose. In general, the therapeutically-effective compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

The activity of the compounds of the present invention, as anti-ulcer agents, is determined by their ability to pass at least one of the following two standard biological and/or pharmacological tests, viz., (1) measuring their ability to antagonise those particular actions of histamine which are not blocked by an antihistamine such as mepyramine, i.e., a measure of their ability to block certain histamine $H_2$-receptor sites; and (2) measuring their ability to inhibit gastric acid secretion in the stomachs of Heidenhain pouch dogs that had previously been treated with pentagastrin in order to stimulate the secretion of said acid (in their stomachs) for these particular purposes.

PREPARATION A

A mixture consisting of 35.8 g. (0.2086 mole) of 2-chloroisonicotinic acid hydrazide and 58.4 g. (0.4196 mole) of 2-methyl-2-thiopseudourea sulfate was suspended in a solution of 8.4 g. (0.21 mole) of sodium hydroxide dissolved in 250 ml of water. The resulting slurry was then stirred at 25° C. for a period of 20 hours and filtered. The light tan solid product so obtained was then washed on the filter funnel with water and thereafter with diethyl ether. After air drying to constant weight, there were ultimately obtained 44.5 g. (95%) of pure 2-chloroisonicotinic acid 2-amidinohydrazide, m.p. 198°–200° C. (with resolidification at 204° C. and subsequent remelting at 233°–234° C.). The final product was subsequently characterized by means of infrared absorption spectroscopy.

PREPARATION B

A mixture consisting of 1.97 g. (0.0129 mole) of 2-aminoisonicotinic acid hydrazide and 3.59 g. (0.0258 mole) of 2-methyl-2-thiopseudourea sulfate was dissolved in a solution consisting of 0.56 g. (0.014 mole) of sodium hydroxide in 20 ml of water. The resulting solution was then stirred at 25° C. for a period of 1.5 hours, at the end of which time a precipitate began to form in the clear solution. The resultant slurry was then further stirred at 25° C. for a period of 18.5 hours and finally filtered. The solid product so obtained was then washed on the filter funnel with a small portion of water and thereafter washed with diethyl ether. After air drying to constant weight, there were ultimately obtained 1.58 g. (63%) of pure 2-aminoisonicotinic acid 2-amidinohydrazide, m.p. 175°–177° C. (with resolidification at 184°–185° C. and subsequent remelting at 251° C.). The final product was subsequently characterized by means of infrared absorption spectroscopy.

PREPARATION C

A mixture consisting of 6.5 g. (0.039 mole) of 2-(N-monomethylamino)isonicotinic acid hydrazide and 10.5 g. (0.075 mole) of 2-methyl-2-thiopseudourea sulfate was placed in a solution consisting of 1.5 g. (0.037 mole) of sodium hydroxide dissolved in 100 ml. of water. The resulting solution was then stirred at 25° C. for a period of 24 hours. The precipitate obtained in this manner was subsequently recovered by means of suction filtration, washed well with water and then air dried to constant weight. In this way, there were ultimately obtained 2.9 g. (35%) of pure 2-(N-monomethylamino)isonicotinic acid 2-amidinohydrazide which was subsequently characterized by means of infrared absorption spectroscopy.

PREPARATION D

A mixture consisting of 6.6 g. (0.0366 mole) of 2-(N-monoethylamino)isonicotinic acid hydrazide and 10.0 g. (0.0718 mole) of 2-methyl-2-thiopseudourea sulfate was placed in a solution consisting of 1.43 g. (0.0366 mole) of sodium hydroxide dissolved in 30 ml. of water. The resulting mixture was then stirred at 25° C. for a period of five hours. At this point, an additional 5.0 g. (0.0359 mole) of 2-methyl-2-thiopseudourea sulfate were added to the mixture and the resultant slurry was thereafter stirred at 25° C. for a further 20 hours. The solid precipitate so obtained was then recovered by means of suction filtration, washed well with water and then with diethyl ether. After air drying to constant weight, there were ultimately obtained 6.1 g. (93%) of pure 2-(N-monoethylamino)isonicotinic acid 2-amidinohydrazide which was subsequently characterized by means of infrared absorption spectroscopy.

PREPARATION E

A mixture consisting of 5.5 g. (0.030 mole) of 2-(N,N-dimethylamino)isonicotinic acid hydrazide and 8.5 g. (0.060 mole) of 2-methyl-2-thiopseudourea sulfate was placed in a solution consisting of 1.2 g. (0.030 mole) of sodium hydroxide dissolved in 30 ml. of water. The resulting solution was then stirred at 25° C. for a period of one hour, during which time a precipitate soon formed. Stirring was then continued at this point for another five hours, followed by the addition of another 4.0 g. (0.014 mole) of 2-methyl-2-thiopseudourea sulfate to the stirred mixture. The resultant slurry was then allowed to stir at 25° C. for a period of 20 hours. The precipitate so obtained was thereafter recovered by means of suction filtration, and washed and dried in the usual manner. In this way, there were ultimately obtained 3.1 g. (46%) of pure 2-(N,N-dimethylamino)isonicotinic acid 2-amidinohydrazide, m.p. 254°–256° C. The final product was subsequently characterized by means of infrared absorption spectroscopy.

PREPARATION F

A mixture consisting of 20.0 g. (0.127 mole) of 2-chloroisonicotinic acid and 100 ml. of isopropylamine was placed in a steel tube containing 400 mg. of copper powder and 100 ml. of water. The resulting mixture was then heated at 170° C. for a period of 48 hours and finally at 210° C. for a period of 24 hours. Upon completion of the reaction, the contents of the tube were cooled to room temperature (~25° C.) and the spent reaction mixture was subsequently acidified to yield a crude solid material that was thereafter collected by means of suction filtration. In this way, there was easily obtained a 4.0 g. yield of crude 2-(N-monoisopropylamino)isonicotinic acid, m.p. 275°–280° C.

PREPARATION G

A mixture consisting of 20 g. (0.127 mole) of 2-chloroisonicotinic acid and 30 g. (0.220 mole) of 2,2,2-trifluoroethylamine hydrochloride was placed in a sealed steel tube which also contained 13.8 g. (0.347 mole) of sodium hydroxide dissolved in 70 ml. of water. The contents of the tube were then heated at 160° C. for a period of 18 hours. Upon completion of the reaction, the contents were cooled to room temperature (~25° C.) and the spent reaction mixture was diluted with water, i.e., up to a total volume of 500 ml. The resulting precipitate was then collected by means of suction filtration and was subsequently triturated with diethyl ether/methanol to afford 6.8 g. (24%) of pure 2-(2,2,2-trifluoroethylamino)isonicotinic acid, m.p. 300°–302° C. The final product was subsequently characterized by means of infrared absorption spectroscopy.

A 6.0 g. (0.027 mole) sample of 2-(2,2,2-trifluoroethylamino)isonicotinic acid (prepared as described above) was added to 200 ml. of an etheral solution of diazomethane, which had earlier been freshly prepared from 25 g. (0.17 mole) of N-methyl-N'-nitro-N-nitrosoguanidine in a conventional manner. After allowing the etheral reaction mixture to stand at 25° C. for a period of one hour, 100 ml. of methanol were added to the mixture and the resultant slurry was gently stirred for 20 hours. At the end of this time, the stirred slurry was carefully filtered into 50 ml. of 1 N aqueous hydrochloric acid to give a clear solution. Concentration of the latter aqueous solution in vacuo then gave 6.8 g. of pure 2-(2,2,2-trifluoroethylamino)isonicotinic acid methyl ester hydrochloride, which was subsequently characterized by means of nuclear magnetic resonance data.

The entire yield (6.8 g., 0.025 mole) of 2-(2,2,2-trifluoroethylamino)isonicotinic acid methyl ester hydrochloride (prepared as described in the above manner) was then combined with 70 ml. of 85% hydrazine hydrate and the resulting mixture gently warmed to the reflux point to afford a clear solution. The solution was then cooled to room temperature ($\sim 25°$ C.) and subsequently concentrated in vacuo to ultimately yield crude 2-(2,2,2-trifluoroethylamino)isonicotinic acid hydrazide as attested to by thin layer chromatography (the silica gel/ethyl acetate eluant had an $R_f$ value of 0.20).

PREPARATION H

To a solution consisting of 1.24 g. (0.031 mole) of sodium hydroxide in 150 ml. of water, there were successively added 8.34 g. (0.030 mole) of S-methylthiopseudourea sulfate and 5.15 g. (0.030 mole) of 2-chloroisonicotinic acid hydrazide (in that order). The resulting heterogeneous mixture was then stirred at room temperature ($\sim 25°$ C.) for a period of 24 hours and finally filtered. The solid product collected in this manner was then washed well on the filter funnel with water and was subsequently dried in vacuo to constant weight to afford 5.8 g. (90%) of pure 2-chloroisonicotinic acid 2-amidinohydrazide, m.p. 203° C. (with resolidification at 204° C. and subsequently remelting at 239° C.). The final product was subsequently characterized by means of nuclear magnetic resonance data.

A 10 g. (0.0468 mole) sample of 2-chloroisonicotinic 2-amidinohydrazide (prepared as described above) was placed in a sublimation apparatus and heated at 210° C. under high vacuum (0.05 torr) for a period of 14 hours. The small amount of material that actually sublimed was then discarded and the remaining material was triturated with cold methanol in order to remove some solid impurities. Concentration of the resulting methanolic filtrate then gave 4.8 g. (53%) of pure 3-amino-5-(2-chloro-4-pyridyl)-1,2,4-triazole as a white solid, m.p. 232°–235° C. An analytically pure sample in the form of a white powder (m.p. 237°–238° C.) was prepared by column chromatography over silica gel using ethyl acetate/methanol (4:1 by volume) as the eluant. The pure final product was subsequently characterized by means of nuclear magnetic resonance data.

PREPARATION I

A solid sample consisting of 12.5 g. (0.05 mole) of 2,6-dichloroisonicotinic acid 2-amidinohydrazide was heated in a round-bottomed reaction flask at 250° C. for a period of 15 minutes, followed by an additional heating period at 270° C. for another 15 minutes. On cooling the spent reaction mixture to near room temperature, i.e., 25° C., the melt soon solidified to yield crude 3-amino-5-(2,6-dichloro-4-pyridyl)-1,2,4-triazole in the form of a light tan solid, m.p. 240°–250° C. The product was subsequently characterized by means of thin layer chromatography (the silica gel/ethyl acetate eluate had an $R_f$ value of 0.38).

EXAMPLE I

A mixture consisting of 10 g. (0.0468 mole) of 2-chloroisonicotinic acid 2-amidinohydrazide (prepared as described in Preparation A) and 100 ml. of 50% aqueous n-propylamine was placed in a 300 ml. steel tube and heated at 160° C. for a period of 38 hours. Upon completion of the reaction, the contents of the tube involving the spent reaction mixture were cooled to room temperature ($\sim 25°$ C.) and then concentrated in vacuo to afford a crude solid residue. The latter material was subsequently triturated with water, dried and thereafter taken up in ethyl acetate/methanol. Filtration of the latter organic solution through a short column of Florisil (the registered trademark name of The Floridin Company of Tallahasee, Fla. for a synthetic magnesia-silica gel consisting essentially of activated magnesium silicate made according to the specifications of U.S. Pat. No. 2,393,625), followed by concentration of the resulting filtrate under reduced pressure then gave a solid product, which was subsequently triturated with hot ethyl acetate and then recrystallized from water to yield 844 mg. (8%) of pure 3-amino-5-{2-[N-mono(n-propyl)amino]-4-pyridyl}-1,2,4-triazole, mp 188°–191° C. The final product was thereafter characterized via nuclear magnetic resonance data.

EXAMPLE II

The procedure described in Example I was repeated except that n-hexylamine (using 100 ml. of a 50% aqueous solution) was the reagent employed in place of n-propylamine and the reaction was conducted at 170° C. for a period of 17 hours. Upon completion of the reaction, the contents of the tube were cooled to room temperature ($\sim 25°$ C.) and then diluted with water to form a two-phase system. The upper layer was separated and then concentrated in vacuo to afford a brown oil, which was subsequently chromatographed on a silica gel column using ethyl acetate/methanol (85:15 by volume) as the eluant to give 3.6 g. of crude product (m.p. 151°–153° C.) and 568 mg. (4.6%) of pure 3-amino-5-{2-[N-mono(n-hexyl)amino]-4-pyridyl}-1,2,4-triazole, m.p. 154°–157° C. The pure final product was then characterized by nuclear magnetic resonance data.

EXAMPLE III

The procedure described in Example I was repeated except that n-decylamine (using 40 ml. of said reagent in 100 ml. of water) was the reagent employed in place of n-propylamine and the reaction was conducted at 165° C. for a period of 48 hours. Upon completion of the reaction, the contents of the tube were cooled to room temperature ($\sim 25°$ C.) and the resulting semi-solids were allowed to stand (at the same said temperature) for a period of 18 days. At this point, a solid substance had formed and the latter material was subsequently collected on a filter funnel by means of suction filtration and thereafter washed with diethyl ether. After one recrystallization from ethyl acetate/methanol, there were ultimately obtained 2.1 g. (14%) of pure 3-amino-5-{2-[N-mono(n-decyl)amino]-4-pyridyl}-1,2,4-triazole, m.p. 152°–154° C. The final product was subsequently characterized by means of nuclear magnetic resonance data.

EXAMPLE IV

The procedure described in Example I was repeated except that allylamine (using 100 ml. of a 50% aqueous solution) was the reagent employed in place of n-propylamine and the reaction was conducted at 170° C. for a period of 22 hours. Upon completion of the reaction, the contents of the tube were cooled to room temperature (~25° C.) and the spent reaction mixture was subsequently concentrated in vacuo to afford a crude residue that was thereafter chromatographed on a silica gel column using ethyl acetate/methanol (95:5 by volume) as the eluant. In this way, there was ultimately obtained a 779 mg. (7.7%) yield of pure 3-amino-5-[2-monoallylamino)-4-pyridyl]-1,2,4-triazole, m.p. 198°–200° C. The final product was then characterized by means of nuclear magnetic resonance data.

EXAMPLE V

The procedure described in Example I was repeated except that 2-aminoethanol (using 2.9 ml. or 0.0478 mole) of said reagent in 100 ml. of water) was the reagent employed in place of n-propylamine and the reaction was conducted at 170° C. for a period of 20 hours. Upon completion of the reaction, the contents of the tube were cooled to room temperature (~25° C.) and the pH of the resulting reaction mixture was adjusted to pH 9.0 with the aid of 1 N aqueous sodium hydroxide solution. The basified aqueous mixture was then concentrated in vacuo to afford a crude waxy solid, which was subsequently chromatographed on a silica gel column using ethyl acetate/methanol (85:15 by volume) as the eluant. In this way, there was obtained a crude product which after one recrystallization from ethyl acetate/methanol ultimately gave 276 mg. (2.6%) of pure 3-amino-5-{2-[N-mono(β-hydroxyethyl)amino]-4-pyridyl}-1,a,4-triazole, m.p. 223°–225° C. The final product was subsequently characterized by means of nuclear magnetic resonance data.

EXAMPLE VI

The procedure described in Example I was repeated except that 3-amino-1-propanol (using 3.6 ml. or 0.0479 mole of said reagent in 100 ml. of water) was the reagent employed in place of n-propylamine and the reaction was conducted at 170° C. for a period of 21 hours. Upon completion of the reaction, the contents of the tube were cooled to room temperature (~25° C.) and the pH of the resulting reaction mixture was adjusted to pH 9.0 with the aid of 1 N aqueous sodium hydroxide. The basified aqueous mixture was then concentrated in vacuo to afford a crude oil, which was subsequently chromatographed on a silica gel column using ethyl acetate/methanol (9:1 by volume) as the eluant. In this way, there was ultimately obtained 114 mg. (1%) of pure 3-amino-5-{2-[N-mono(γ-hydroxypropyl)amino]-4-pyridyl}-1,2,4-triazole, m.p. 216°–218° C. The final product was subsequently characterized by means of mass spectroscopy.

EXAMPLE VII

The procedure described in Example I was repeated except that 2-methoxyethylamine (using 100 ml of a 50% aqueous solution) was the reagent employed in place of n-propylamine and the reaction was conducted at 170° C. for a period of 64 hours. Upon completion of the reaction, the contents of the tube were cooled to room temperature (~25° C.) and the spent reaction mixture was subsequently concentrated in vacuo to afford a crude residue that was thereafter chromatographed on a silica gel column using ethyl acetate/methanol (4:1 by volume) as the eluant. In this way, there was obtained a crude product which after one recrystallization from ethyl acetate/methanol ultimately gave 2.48 g. (22%) of pure 3-amino-5-{2-[N-mono(β-methoxyethyl)amino]-4-pyridyl}-1,2,4-triazole, m.p. 154°–156° C. The final product was subsequently characterized by means of nuclear magnetic resonance data.

EXAMPLE VIII

The procedure described in Example I was repeated except that dimethylamine (using 100 ml. of a 25% aqueous solution) was the reagent employed in place of n-propylamine and the reaction was conducted at 170° C. for a period of 41 hours. Upon completion of the reaction, the contents of the tube were cooled to room temperature (~25° C.) and then quickly removed therefrom, while the resulting empty vessel was thereafter washed with two-successive 50 ml. portions of methanol and two-successive 50 ml. portions of water, respectively. The combined contents (involving the spent reaction mixture) and washings were then passed through a filter and the resulting filtrate was subsequently concentrated in vacuo to afford a crude tan solid material as the residue. The latter substance was finally slurried in a minimum amount of water and then filtered to give 3.95 g. (41%) of pure 3-amino-5-[2-(N,N-dimethylamino)-4-pyridyl]-1,2,4-triazole, m.p. 255°–257° C.

EXAMPLE IX

The procedure described in Example I was repeated except that N-methyl-N-ethylamine (using 14.0 g. or 0.236 mole of said reagent in 100 ml. of water) was the reagent employed in place of n-propylamine and the reaction was conducted at 170° C. for a period of 19 hours. Upon completion of the reaction, the contents of the tube were cooled to room temperature (~25° C.) and then quickly removed therefrom, while the resulting empty vessel was thereafter washed thoroughly with 50 ml of water. The combined contents (i.e., spent reaction mixture) and wash were then filtered and the green filtrate so obtained was subsequently concentrated in vacuo to afford a green oil as the residue. The latter substance was then taken up in water and extracted with two-100 ml. portions of ethyl acetate. The organic extracts (after being combined) were dried over anhydrous sodium sulfate and filtered, and the resulting filtrate was subsequently evaporated to dryness under reduced pressure to give a crude yellow solid. Trituration of the latter material with ethyl acetate/diethyl ether, followed by filtration, then gave 5.49 g. (54%) of pure 3-amino-5-[2-(N-methyl-N-ethylamino)-4-pyridyl]-1,2,4-triazole, m.p. 199°–201° C. The final product was subsequently characterized by means of nuclear magnetic resonance data.

EXAMPLE X

The procedure described in Example I was repeated except that diethylamine (using 100 ml. of a 60% aqueous solution) was the reagent employed in place of n-propylamine and the reaction was conducted at 170° C. for a period of 18 hours. Upon completion of the reaction, the contents of the tube were cooled to room temperature (~25° C.) and the spent reaction mixture was subsequently concentrated in vacuo to afford a crude thick oil that was thereafter chromatographed on a Florisil column using ethyl acetate/methanol (85:15 by volume) as the eluant. In this way, there was obtained a crude product, in the form of a glass, which after recrystallization from water ultimately gave 3.6 g. (33%) of pure 3-amino-5-[2-(N,N-diethylamino)-4-pyridyl]-1,2,4-triazole, m.p. 193°–196° C. The final product was subsequently characterized by means of nuclear magnetic resonance data.

EXAMPLE XI

The procedure described in Example I was repeated except that 60 g. (0.963 mole) of 2-chloroisonicotinic acid 2-amidinohydrazide and 600 ml. of 70% aqueous ethylamine were reacted at 160° C. for a period of 40 hours. Upon completion of the reaction, the contents of the tube were cooled to room temperature (~25° C.) and the spent reaction mixture was subsequently concentrated in vacuo to afford a thick syrup that was thereafter chromatographed on a silica gel column using chloroform/methanol as the eluant. The first fraction collected in this manner was saved and subsequently stripped of solvent by means of evaporation under reduced pressure to give a crude solid. Trituration of the latter material with ethyl acetate/methanol, followed by filtration, then gave a white solid on the filter funnel and a dark organic solution as the filtrate. The filtrate was saved and subsequently evaporated to dryness while under reduced pressure to yield 36.1 g. of a crude oil. The latter material (oil) was then chromatographed on silica gel using ethyl acetate/methanol (95:5 by volume) as the eluant to afford a crude white solid. Trituration of the latter product with ethyl acetate/diethyl ether and then with methanol finally gave 369 mg. (0.165%) of pure 3-(monoethylamino)-5-[2-(N-monoethylamino)-4-pyridyl]-1,2,4-triazole, m.p. 224°-226° C. The final product was subsequently characterized by means of nuclear magnetic resonance data.

EXAMPLE XII

The procedure described in Example I was repeated except that 6.4 g. (0.03 mole) of 2-chloroisonicotinic acid 2-amidinohydrazide and 100 ml. of 20% aqueous $\beta$-phenylethylamine (20 ml. of said reagent in 80 ml. of water) were reacted at 175° C. for a period of 40 hours. Upon completion of the reaction, the contents of the tube were cooled to room temperature (~25° C.) and the spent reaction mixture was subsequently extracted with 60 ml. of ethyl acetate. The organic extract so obtained was then dried over anhydrous sodium sulfate, filtered and the resulting filtrate thereafter evaporated to dryness while under reduced pressure to afford a crude oil. Trituration of the latter oil with 200 ml. of toluene, followed by scratching with a glass rod, then gave a solid product which was subsequently dried in vacuo to constant weight. In this way, there was ultimately obtained pure 3-amino-5-{2-[N-mono($\beta$-phenylethyl)amino]-4-pyridyl}-1,2,4-triazole, m.p. 183°-184° C. after recrystallization from water. The yield of pure product amounted to 3.0 g. (36%) and was subsequently characterized by means of mass spectroscopy.

EXAMPLE XIII

The procedure described in Example I was repeated except that 2-amino-1-phenylethanol (using 6.5 g. or 0.0474 mole of said reagent in 100 ml. of water) was the reagent employed in place of n-propylamine and the reaction was conducted at 170° C. for a period of 40 hours. Upon completion of the reaction, the contents of the tube were cooled to room temperature (~25° C.) and then quickly removed therefrom, while the resulting empty vessel was thereafter washed with a small portion of water. The combined contents (i.e., spent reaction mixture) and wash were then filtered and the resulting filtrate was subsequently concentrated in vacuo to afford a crude yellow solid as the residue. The latter substance was then chromatographed on silica gel using ethyl acetate/methanol (95:5 by volume) as the eluant to yield 2.6 g. of 3-amino-5-(2-chloro-4-pyridyl)-1,2,4-triazole (m.p. 201°-203° C.) and 0.541 g. (3.9%) of pure 3-amino-5-{2-[N-mono($\beta$-phenyl-$\beta$-hydroxyethyl)amino]-4-pyridyl}-1,2,4-triazole, mp 201°-203° C. The pure final product was subsequently characterized by means of nuclear magnetic resonance data.

EXAMPLE XIV

The procedure described in Example I was repeated except that 1.20 g. (0.0056 mole) of 2-chloroisonicotinic acid 2-amidinohydrazide and 10 ml. of benzylamine were reacted in 15 ml. of water at 185° C. for a period of 40 hours. Upon completion of the reaction, the contents of the tube were cooled to room temperature (~25° C.) and then removed therefrom, followed by concentration of same under reduced pressure to afford a residue. The latter material was then partitioned between 50 ml. of ethyl acetate and 50 ml. of water, and the ethyl acetate layer was subsequently collected and dried over anhydrous sodium sulfate. After removal of the drying agent by means of filtration and the solvent by means of evaporation under reduced pressure, there was obtained an oily residue which was taken up in diethyl ether with stirring. The oil was treated in this manner for a period of approximately one hour, during which time it soon solidified. The solid material so obtained was then chromatographed on silica gel using chloroform/methanol (19:1 by volume) as the eluant to ultimately afford 650 mg. (44%) of pure 3-amino-5-[2-(N-monobenzylamino)-4-pyridyl]-1,2,4-triazole in the form of a white fluffy glass-like solid, m.p. 115° C. (decomp.). The final product was subsequently characterized by both mass spectroscopy and nuclear magnetic resonance data.

EXAMPLE XV

The procedure described in Example I was repeated except that 1.20 g. (0.0056 mole) of 2-chloroisonicotinic acid 2-amidinohydrazide and 8 ml of p-chlorobenzylamine were reacted in 20 ml. of water at 75° C. for a period of 60 hours. Upon completion of the reaction, the contents of the tube were cooled to room temperature (~25° C.) and the spent reaction mixture was subsequently extracted with 50 ml. of ethyl acetate. The organic extract so obtained was then dried over anhydrous sodium sulfate, filtered and the resulting filtrate thereafter evaporated to dryness while under reduced pressure to afford a crude oil. The latter substance was then chromatographed on silica gel using chloroform/methanol (19:1 by volume) as the eluant to yield 720 mg. (43%) of pure 3-amino-5-{2-[N-mono(p-chlorobenzyl)amino]-4-pyridyl}-1,2,4-triazole in the form of a white solid, m.p. 176°-177° C. after one recrystallization from acetonitrile-toluene. The pure final product (m.p. 176°-177° C.) was subsequently characterized by means of nuclear magnetic resonance data.

EXAMPLE XVI

The procedure described in Example I was repeated except that 1.20 g. (0.0056 mole) of 2-chloroisonicotinic acid 2-amidinohydrazide and 5 ml. of p-methylbenzylamine were reacted in 20 ml. of water at 175° C. for a period of 48 hours. Upon completion of the reaction, the contents of the tube were cooled to room temperature (~25° C.) and the spent reaction mixture was subsequently extracted with 50 ml. of ethyl acetate. The organic extract so obtained was then dried over anhydrous sodium sulfate, filtered and the resulting filtrate thereafter evaporated to dryness while under reduced pressure to afford an oil as the residual material. The latter substance was then chromatographed on silica gel using chloroform/methanol (19:1 by volume) as the eluant to yield 1.8 g. of an amber-colored oil, which was thereafter slowly dissolved in 2 ml. of hot acetonitrile. Treatment of the latter solution with 5 ml. of toluene, followed by cooling then gave a solid precipitate consisting essentially of crude product. After two recrystallizations from acetonitrile/toluene, there was finally obtained 518 mg. (33%) of pure 3-amino-5-{2[N-mono-p-methylbenzyl)amino]-4-pyridyl}-1,2,4-triazole in the form of a white solid material, m.p. 161.5°-162.5° C. The pure final product was subsequently characterized by means of nuclear magnetic resonance data.

EXAMPLE XVII

The procedure described in Example I was repeated except that 1.20 g. (0.0056 mole) of 2-chloroisonicotinic acid 2-amidinohydrazide and 5 ml. of p-methoxybenzylamine were reacted in 20 ml. of water at 175° C. for a period of 48 hours. Upon completion of the reaction, the contents of the tube were cooled to room temperature (~25° C.) and the spent reaction mixture was subsequently extracted with 50 ml. of ethyl acetate. The organic extract so obtained was then dried over anhydrous sodium sulfate, filtered and the resulting filtrate thereafter evaporated to dryness while under reduced pressure to afford an oil as the residual material. The latter substance was then chromatographed in silica gel using chloroform/methanol (19:1 by volume) as the eluant to give 1.0 g. of an oil, which was subsequently dissolved in 2 ml. of hot acetonitrile. Treatment of the latter solution with toluene, as in the previous example, then gave a precipitate consisting essentially of crude final product. The latter material was subsequently recovered by means of suction filtration and dried in vacuo to constant weight. After recrystallization from acetonitrile/toluene, there was finally obtained 352 mg. (21%) of pure 3-amino-5-{2-[N-mono(p-methoxybenzyl)amino]-4-pyridyl}-1,2,4-triazole in the form of a white solid, m.p. 136°-139° C. The pure final product was subsequently characterized by means of nuclear magnetic resonance data.

EXAMPLE XVIII

A sample consisting of 1.15 g. (0.007 mole) of pure 2-aminoisonicotinic acid 2-amidinohydrazide monohydrate (prepared as described in Preparation B) was placed in a suitable reaction flask and heated at 185° C. for a period of one hour. The solid substance so obtained was then cooled to room temperature (~25° C.) to give a tan-colored product melting at 244°-246° C. Recrystallization of the latter material from water then gave 760 mg. (56%) of pu re 3-amino-5-(2-aminopyridyl)-1,2,4-triazole monohydrate, m.p. 246°-247° C. The final product was subsequently characterized by means of nuclear magnetic resonance data.

EXAMPLE XIX

A sample consisting of 2.9 g. (0.0139 mole) of pure 2-(N-monomethylamino)isonicotinic acid 2-amidinohydrazide (prepared as described in Preparation C) was placed in a suitable reaction vessel and heated at 230° C. for a period of ten minutes. The solid substance so obtained was then cooled to room temperature (~25° C.) and recrystallized from ethyl acetate/methanol to ultimately yield 1.1 g. (38%) of pure 3-amino-5-[2-(N-monomethylamino)-4-pyridyl]-1,2,4-triazole, m.p. 261°-263° C. The final product was subsequently characterized by means of nuclear magnetic resonance data.

EXAMPLE XX

A sample consisting of 6.1 g. (0.0274 mole) of pure 2-(N-monoethylamino)isonicotinic acid 2-amidinohydrazide (prepared as described in Preparation D) was placed in a suitable reaction vessel and heated rapidly to 270° C., followed by cooling to 225° C. It was then held at the latter point (via renewed heating) for a period of five minutes. On cooling the resulting reaction mass to room temperature (~25° C.), the solid product so obtained was thereafter recrystallized from methanol/ethyl acetate to give 1.2 g. (21%) of pure 3-amino-5-[2-(N-monoethylamino)-4-pyridyl]-1,2,4-triazole. Differential thermal analysis showed equally sharp endothermic transitions at both 255° C. and 260° C. The pure final product was subsequently characterized by means of nuclear magnetic resonance data.

EXAMPLE XXI

A sample consisting of 3.1 g. (0.014 mole) of pure 2-(N,N-dimethylamino)isonicotinic acid 2-amidinohydrazide (prepared as described in Preparation E) was placed in a suitable reaction flask and slowly heated to 270° C. while under a nitrogen atmosphere. On cooling the resulting reaction mass to room temperature (~25° C.), the solid product so obtained was thereafter recrystallized from ethyl acetate/methanol to afford 470 mg. (16%) of pure 3-amino-5-[2-(N,N-dimethylamino)-4-pyridyl]-1,2,4-triazole, m.p. 257°-260° C. The final product was subsequently characterized by means of nuclear magnetic resonance data.

EXAMPLE XXII

A mixture consisting of 2.5 g. (0.0108 mole) of 2-[N-mono(n-butyl)-amino]isonicotinic acid and 2.7 g. (0.0219 mole) of aminoguanidine sulfate was placed in a suitable reaction flask and heated at 200° C. for a period of three hours while under a nitrogen atmosphere. The melt was then cooled to room temperature (~25° C.), diluted with water and the pH of the resulting mixture adjusted to pH 8.0 with 1 N aqueous sodium hydroxide. The basified aqueous mixture was next filtered and the clear aqueous filtrate so obtained was subsequently concentrated in vacuo to afford a brown oil, which was thereafter triturated with methanol. After removal of the resultant solid by means of suction filtration, ethyl acetate was added to the filtrate and the latter solution was subsequently concentrated on a steam bath, followed by cooling to room temperature. In this way, there were ultimately isolated 1.04 g. of crude product (m.p. 218°-220° C.) in the form of a beige-colored precipitate. Recrystallization of the latter material from ethyl acetate/methanol then gave 467 mg (18%) of pure 3-amino-5-{2-[N-mono(n-butyl)amino]-4-pyridyl}-1,2,4-triazole, m.p. 268°-270° C. The final product was subsequently characterized by means of nuclear magnetic resonance data.

EXAMPLE XXIII

A mixture consisting of 4.0 g. (0.022 mole) of crude 2-(N-monoisopropylamino)isonicotinic acid (prepared as described in Preparation F) and 5.5 g. (0.044 mole) of aminoguanidine sulfate was heated at 200° C. for a period of nine hours according to the procedure of Example XXII. Upon completion of the reaction, the contents of the flask were cooled to room temperature (~25° C.) and the resulting residue was diluted with water prior to adjusting the pH of the mixture to 7.0 with 1 N aqueous sodium hydroxide. The basic aqueous solution so obtained was then extracted with ethyl acetate and the latter organic extracts were subsequently combined, dried and then concentrated in vacuo to afford a glass as the solid residue. Trituration of the latter material with ethyl acetate then gave a crude solid material, which was subsequently crystallized from hot ethyl acetate to afford 1.07 g. (22%) of pure 3-amino-5-[2-(N-monoisopropylamino)-4-pyridyl]-1,2,4-triazole, m.p. 185°–186° C. The pure final product was subsequently characterized by means of nuclear magnetic resonance data.

EXAMPLE XXIV

A mixture consisting of 13.55 g. (0.0609 mole) of 2-(N,N-dimethylamino)isonicotinic acid and 15.0 g. (0.1219 mole) of aminoguanidine sulfate was heated essentially according to the procedure described in Example XXII. At 150°–160° C., the reaction mixture first melted but as the temperature was raised to 200° C., it solidified again. Finally, after heating at 200° C., for a period of seven hours, the reaction mixture was cooled to room temperature (~25° C.) and then treated with 1 N aqueous sodium hydroxide solution until the pH of the resulting mixture was raised to pH 9.0. At this point, the solvent was removed in vacuo and the residue thereafter triturated with methanol and filtered. The filtrate so obtained was saved and thereafter concentrated in vacuo to afford a crude solid, which was subsequently passed through a column of Florisil 60/100A (the registered trademark name of The Floridin Company of Tallahasee, Florida for a synthetic magnesia-silica gel consisting essentially of activated magnesium silicate made according to the specifications of U.S. Pat. No. 2,393,625) using chloroform/methanol (9:1 by volume) as the eluant in order to remove polar impurities. The resulting crude product was then recrystallized from ethyl acetate/methanol to yield 2.15 g. (17%) of pure 3-amino-5-[2-(N,N-dimethylamino)-4-pyridyl]-1,2,4-triazole, m.p. 257°–260° C. This product was identical in every respect with that produced in Examples VIII and XXI, respectively.

EXAMPLE XXV

A mixture consisting of 3.6 g. (0.0154 mole) of 2-(2,2,2-trifluoroethylamino)isonicotinic acid hydrazide (prepared according to the procedure described in Preparation G) and 3.11 g. (0.0153 mole) of 2-benzyl-2-thiopseudourea hydrochloride was suspended in a solution of 20 ml. of 50% aqueous dioxane (i.e., 10 ml. of water and 10 ml. of dioxane). The resultant slurry was then adjusted to pH 9.5–10 with the aid of 20% aqueous sodium hydroxide and stirred at 25° C. for a period of 96 hours. During this time, six-1.0 g. portions of 2-benzyl-2-thiopseudourea hydrochloride were further added to the mixture and with each addition the pH was once again adjusted to pH 9.5–10 with 20% aqueous sodium hydroxide. Upon completion of this step, the entire reaction mixture was eluted through a Florisil column using ethyl acetate/methanol as the eluant. The crude product so obtained in this manner was then recrystallized from ethyl acetate/methanol to give 1.5 g. (38%) of pure 3-amino-5-{2-[N-mono(2,2,2-trifluoroethyl)amino]-4-pyridyl}-1,2,4-triazole, m.p. 198°–200° C. The final product was subsequently characterized by means of nuclear magnetic resonance data.

EXAMPLE XXVI

A mixture consisting of 8.0 g. (0.0444 mole) of 2-(N-monoethylamino)isonicotinic acid hydrazide and 10.3 g. (0.0444 mole) of N-methyl-S-methylthiopseudourea hydriodide was placed in a solution of 1.77 g. (0.0444 mole) of sodium hydroxide in 50 ml. of water. The resulting mixture was then heated at the reflux point for a period of 22 hours, cooled to room temperature (~25° C.) and filtered. The recovered solid product was subsequently dried in vacuo to constant weight and there were ultimately obtained 1.9 g. (19%) of pure 3-(N-monomethylamino)-5-[2-(N-monoethylamino)-4-pyridyl]-1,2,4-triazole, m.p. 273°–276° C. The pure final product was subsequently characterized by means of nuclear magnetic resonance data.

EXAMPLE XXVII

A mixture consisting of 1.0 g. (0.0051 mole) of 3-amino-5-(2-chloro-4-pyridyl)-1,2,4-triazole (prepared according to the procedure described in Preparation H) and 5.0 ml of β-phenylethylamine in 15 ml. of water was placed in a steel tube and heated at 175° C. for a period of 15 hours. Upon completion of the reaction, the contents of the tube were cooled to room temperature (~25° C.) and then rendered homogeneous by the addition of acetone. The resulting solution was then concentrated in vacuo and the residue so obtained was partitioned between ethyl acetate/water. The ethyl acetate layer was separated and saved, followed by drying over anhydrous sodium sulfate. After removal of the drying agent by means of filtration and the solvent by means of evaporation under reduced pressure, there was finally obtained an oil which solidified on trituration with toluene plus the aid of scratching with a glass rod. Recrystallization of the latter solid material from water then gave 0.69 g. (49%) of pure 3-amino-5-{2-[N-mono(β-phenylethyl)amino]-4-pyridyl}-1,2,4-triazole (m.p. 182°–184° C.) in the form of a white crystalline solid. The final product was subsequently characterized by means of mass spectroscopy.

EXAMPLE XXVIII

A mixture consisting of 1.20 g. (0.056 mole) of 2-chloroisonicotinic acid 2-amidinohydrazide (prepared as described in Preparation A), 5.0 ml. of 3,4-dimethylbenzylamine and 20 ml. of water was placed in a steel tube and heated at 160° C. for a period of 75 hours. Upon completion of the reaction, the contents of the tube were cooled to room temperature (~25° C.) and then extracted with 50 ml. of chloroform. The chloroform extract was dried over anhydrous sodium sulfate and filtered, and the resulting filtrate was subsequently concentrated in vacuo to afford a brown oil. The latter oil was then chromatographed over a silica gel column using chloroform/methanol (19:1 by volume) as the eluant to afford a colorless oil. The colorless (i.e., purified) oil so obtained was then taken up in 10 ml. of hot chloroform to which 5 ml. of n-hexane was slowly added. After scratching in the usual manner with a glass rod, the desired product soon precipitated from solution in the form of white crystalline solid. Recrystallization of the latter material (488 mg. melting at 103°–110° C.)

from chloroform/isopropyl ether then gave 210 mg. (13%) of pure 3-amino-5-{2-[N-mono(3',4'-dimethylbenzyl)amino]-4-pyridyl}-1,2,4-triazole, m.p. 125°–127° C. The pure final product was subsequently characterized by means of nuclear magnetic resonance data.

EXAMPLE XXIX

A mixture consisting of 1.20 g. (0.0056 mole) of 2-chloroisonicotinic acid 2-amidinohydrazide (prepared as described in Preparation A), 3.5 ml. of p-tert-butylbenzylamine and 20 ml. of water was placed in a steel tube and heated at 175° C. for a period of 75 hours. Upon completion of the reaction, the contents of the tube were cooled to room temperature (~25° C.) and then shaken with chloroform which resulted in the precipitation of a solid substance from the two-phase system. The latter solid, which was then collected by means of suction filtration and air dried to constant weight, amounted to 650 mg. and melted at 305°–306° C. Recrystallization of the latter material from chloroform/methanol (1:1 by volume) then gave 450 mg. (23%) of pure 3-amino-5-{2-[N-mono(p-tert-butylbenzyl)amino]-4-pyridyl}-1,2,4-triazole in the form of a white solid, m.p. 306°–307° C. The pure final product (m.p. 306°–307° C.) was subsequently characterized by means of nuclear magnetic resonance data.

EXAMPLE XXX

An intimate mixture consisting of 913 mg. (0.006 mole) of 2-amino-6-methylisonicotinic acid and 1.11 g. (0.0045 mole) of aminoguanidine sulfate was placed in a suitable reaction flask and heated at 205° C. for a period of 16 hours while under a nitrogen atmosphere. Upon completion of the reaction, the contents of the flask were cooled to room temperature (~25° C.) and the spent reaction mixture was subsequently treated with 50 ml. of saturated aqueous sodium bicarbonate solution. The basified aqueous mixture so obtained was next filtered and the resulting filtrate thereafter concentrated in vacuo to afford a semi-solid residue. Trituration of the latter material with hot methanol, followed by filtration, then gave an oil in the form of the filtrate. The latter oil was then concentrated in vacuo and subsequently chromatographed over 40 g. of silica gel using 5% methanol in ethyl acetate as the eluant to ultimately afford 200 mg. (18%) of pure 3-amino-5-(2-amino-6-methyl-4-pyridyl)-1,2,4-triazole in the form of a yellow solid, m.p. 98°–106° C. The pure final product was subsequently characterized by means of mass spectroscopy as well as by nuclear magnetic resonance data.

EXAMPLE XXXI

A mixture consisting of 2.0 g. (0.0087 mole) of 3-amino-(2,6-dichloro-4-pyridyl)-1,2,4-triazole (prepared according to the procedure described in Preparation I) and 30 ml. of concentrated ammonium hydroxide was placed in a stainless-steel tube and heated at 230° C. for a period of six hours. Upon completion of the reaction, the contents of the tube were cooled to room temperature (~25° C.) and then diluted with 200 ml. of water prior to being filtered. The resulting filtrate was then concentrated in vacuo and the residue was taken up in methanol, which resulted in the precipitation of a crude solid material from said solution. The latter crude material was then subjected to preparation thin layer chromatography on silica gel using a solvent system consisting of four parts by volume of n-propanol and one part by volume of 29% aqueous ammonium hydroxide. The crude 3-amino-5-(2,6-diamino-4-pyridyl)-1,2,4-triazole final product was isolated by removing the major fluorescent band from the silica gel plate (where the $R_f$ value was 0.58) and then eluting the selected sample with methanol. Treatment of the clear methanol extract so obtained with dry hydrogen chloride gas then gave 80 mg. of pure 3-amino-5-(2,6-diamino-4-pyridyl)-1,2,4-triazole as the hydrochloride salt, m.p. >300° C. The pure final product was subsequently characterized by means of mass spectroscopy.

EXAMPLE XXXII

A mixture consisting of 3.0 g. (0.012 mole) of (N-methyl-N-benzylamino)isonicotinic acid and 2.3 g. (0.0093 mole) of aminoguanidine sulfate was placed in a suitable reaction flask and heated at 185° C. for a period of 16 hours while under a nitrogen atmosphere. Upon completion of this step, the contents of the flask were cooled to 25° C. and the spent reaction mixture was subsequently treated with saturated aqueous sodium bicarbonate solution. The basified aqueous mixture was next brought to a boil and filtered while hot, and the solid material so obtained was then collected in the usual manner and subsequently triturated with acetone. After removal of the resultant solid by means of suction filtration, the filtrate was concentrated in vacuo to afford 1.7 g. of crude material (impure product) in the form of a solid form. The latter product was then further purified by means of column chromatography over 40 g. of silica gel using chloroform/ethyl acetate as the eluent. In this manner, there was ultimately obtained 0.44 g. (17%) of pure 3-amino-5-[2-(N-methyl-N-benzylamino)-4-pyridyl]-1,2,4-triazole in the form of a solid foam, m.p. 85° C. The pure final product was subsequently characterized by means of mass spectroscopy.

EXAMPLE XXXIII

The following 3-amino-5-(4-pyridyl)-1,2,4-triazole base compounds are prepared by employing the procedures described in the previous Examples, starting from readily available materials in each instance:

3-amino-5-{2-[N-mono(n-dodecyl)amino]-4-pyridyl}-1,2,4-triazole 3-(N-monomethylamino)-5-{2-[N-mono(n-dodecyl)amino]-4-pyridyl}-1,2,4-trizole 3-(N-monoisopropylamino)-5-[2-(N-monomethylamino)-4-pyridyl]-1,2,4-triazole 3-amino-5-{2-[N-methyl-N-mono-(n-dodecyl)amino]-4-pyridyl}-1,2,4-triazole 3-(N-monoethylamino)-5-[2-amino-6-(n-butyl)-4-pyridyl]-1,2,4-triazole 3-amino-5-[2,6-di(N-monomethylamino)-4-pyridyl]-1,2,4-triazole 3-amino-5-{2-[N-ethyl-N-mono(n-dodecyl)amino]-4-pyridyl}-1,2,4-triazole 3-(N,N-dimethylamino)-5-[2-(N,N-dimethylamino)-4-pyridyl]-1,2,4-triazole 3-[N,N-di(n-propyl)amino]-5-[2-(N-monoethylamino)-4-pyridyl]-1,2,4-triazole 3-(N-monoethylamino)-5-(2-amino-4-pyridyl)-1,2,4-triazole 3-amino-5-{2-[N-methyl-N-(n-dodecyl)amino]-4-pyridyl}-1,2,4-triazole 3-(N-monomethylamino)-5-{2-[N-ethyl-N-(n-dodecyl)amino]-4-pyridyl}-1,2,4-triazole 3-(N-monoethylamino)-5-[2-(N-monoallylamino)-4-pyridyl]-1,2,4-triazole 3-amino-5-[2-N-monomethallylamino)-4-pyridyl]-1,2,4-triazole 3-(N-monoethylamino)-5-{2-[N-β-hydroxyethyl)amino]-4-pyridyl}-1,2,4-triazole 3-(N-monoethylamino)-5-{2-[N-γ-hydroxypropyl)amino]-4-pyridyl}-1,2,4-triazole 3-(N-monoethylamino)-5-{2-[N-γ-ethoxypropyl)amino]-4-pyridyl}-1,2,4-triazole 3-(N-monoethylamino)-5-{2-[N-mono(2,2,2-trifluoroethyl)amino]-4-pyridyl}-1,2,4-triazole 3-(N-monoethylamino)-5-[2-(N-monobenzylamino)-4-pyridyl]-1,2,4-triazole 3-(N-monomethylamino)-5-{2-[N-β-phenylethyl)amino]-4-pyridyl}-1,2,4-triazole 3-(N-monoethylamino)-5-{2-[N-β-phenyl-β-hydroxyethyl)amino]-4-pyridyl}-1,2,4-triazole 3-amino-5-[2-(N-monoethylamino)-6-(N-monoisopropylamino)-4-pyridyl]-1,2,4-triazole 3-(N-monomethylamino)-5-[2-amino-6-(N-monoisopropylamino)-4-pyridyl]-triazole 3-(N-monoethylamino)-5-{2-[N-mono(o-fluorobenzyl)amino]-4-pyridyl}-1,2,4-triazole 3-(N-monomethylamino)-5-{2-[N-mono(m-chloro-β-phenylethyl)amino]-4-pyridyl}-1,2,4-triazole 3-amino-5-{2-[N-mono(p-bromobenzyl)amino]-4-pyridyl}-1,2,4-triazole 3-amino-5-{2-[N-mono(m-trifluoromethyl-β-phenylethyl)amino]-4-pyridyl}-1,2,4-triazole 3-(N-monoethylamino)-5-{2-[N-mono(p-isopropylbenzyl)amino]-4-pyridyl}-1,2,4-triazole 3-(N-monomethylamino)-5-{2-[N-mono(p-ethoxy-β-phenylethyl)amino]-4-pyridyl}-1,2,4-triazole 3-amino-5-{2-[N-mono(2',4'-dichlorobenzyl)amino]-4-pyridyl}-1,2,4-triazole 3-(N,N-dimethylamino)-5-{2-[N-mono(3',4'-dimethoxybenzyl)amino]-4-pyridyl}-1,2,4-triazole 3-(N-monoethylamino)-5-{2-[N-mono(5'-chloro-2'-methoxybenzyl)amino]-4-pyridyl}-1,2,4-triazole 3-(N-monoethylamino)-5-{2-[N-mono(2'-methoxy-5'-methylbenzyl)amino]-4-pyridyl}-1,2,4-triazole 3-amino-5-[2-(N-ethyl-N-benzylamino)-4-pyridyl]-1,2,4-triazole 3-(N,N-dimethylamino)-5-[2-(N-methyl-N-benzylamino)-4-pyridyl]-1,2,4-triazole 3-(N-monoethylamino)-5-{2-[N-ethyl-N-(p-chlorobenzyl)amino]-4-pyridyl}-1,2,4-triazole 3-amino-5-{2-[N-methyl-N-(p-methoxybenzyl)amino]-4-pyridyl}-1,2,4-triazole.

EXAMPLE XXXIV

The non-toxic hydrochloric acid addition salts of each of the previously reported 3-amino-5-(4-pyridyl)-1,2,4-triazole base compounds of this invention, such as the corresponding hydrochloride, hydrobromide and hydroiodide salts, are each individually prepared by first dissolving the respective organic base compound in absolute ether followed by the introduction of the appropriate hydrohlaide gas into the reaction solution until saturation of same is complete with respect to said gas, whereupon the desired acid addition salt soon precipitates from said solution. In this way, 1.0 g. of 3-amino-5-[2-(N,N-dimethylamino)-4-pyridyl]-1,2,4-triazole, obtained as a free base product in Example VIII, is converted via dry hydrogen chloride gas to the corresponding dihydrochloride acid addition salt in substantially quantitative yield.

EXAMPLE XXXV

The nitrite, sulfate or bisulfate, phosphate or acid phosphate, acetate, lactate, maleate, fumarate, citrate or acid citrate, tartrate of bitartrate, succinate, gluconate, saccharate, methanesulfonate, ethanesulfonate, benzenesulfonate and p-toluenesulfonate salts of each of the aforementioned 3-amino-5-(4-pyridyl)-1,2,4-triazole base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition salt therefrom. In this manner, equimolar amounts of 3-amino-5-[2-(N-monoethylamino)-4-pyridyl]-1,2,4-triazole and concentrated sulfuric acid react to afford the corresponding sulfuric acid addition salt. In like manner, each of the other salts if similarly prepared.

EXAMPLE XXXVI

A dry pharmaceutical composition is prepared by blending the following materials together in the proportions by weight specified below:

| | |
|---|---|
| 3-Amino-5-[2-(N,N-dimethylamino)-4-pyridyl]-1,2,4-triazole dihydrochloride | 50 |
| Sodium citrate | 25 |
| Alginic acid | 10 |
| Polyvinylpyrrolidone | 10 |
| Magnesium stearate | 5 |

After the dried composition is thoroughly blended, tablets are punched from the resulting mixture, each tablet being of such size that it contains 200 mg. of the active ingredient. Other tablets are also prepared in a similar fashion containing 25, 50 and 100 mg. of the active ingredient, respectively, by merely using the appropriate amount of the 3-amino-5-(4-pyridyl)-1,2,4-triazole salt in each case.

EXAMPLE XXXVII

A dry solid pharmaceutical composition is prepared by combining the following materials together in the proportions by weight indicated:

| | |
|---|---|
| 3-Amino-5-[2-(N,N-dimethylamino)-4-pyridyl]-1,2,4-triazole dihydrochloride | 50 |
| Calcium carbonate | 20 |
| Polyethylene glycol, average molecular weight 4000 | 30 |

The dried mixture so prepared is then thoroughly agitated so as to obtain a powdered product that is completely uniform in every respect. Soft elastic and hard-filled gelatin capsules containing this pharmaceutical composition are then prepsred, employing a sufficient quantity of material in each instance so as to provide each capsule with 250 mg. of the active ingredient.

EXAMPLE XXXVIII

The following 3-amino-5-(4-pyridyl)-1,2,4-triazole final products of Examples I–V, VII–XII, XIV–XVI, XVIII–XX, XXII–XXIII, XXV–XXVI, XXVIII and XXXII, respectively, were tested for antiulcer activity in terms of their ability to inhibit gastric acid secretion in groups of fasted Heidenhain pouch dogs. No anesthetic was used in this study. The animals were first administered pentagastrin in order to stimulate acid output in their stomachs by the continuous infusion of said drug into a superified leg vein at doses earlier determined to stimulate near maximal acid output from the gastric pouch. Gastric juice was then collected at 30-minute intervals following the start of a pentagastrin infusion amd measured to the nearest one-tenth of a millimeter (0.1 ml.). Ten collections were taken for each dog during an experiment. Acid concentration was then determined by titrating 1.0 ml. of gastric juice to a pH value of pH 7.4 with 0.1 N aqueous sodium hydroxide, using an Autoburette and a glass electrode pH meter (Radiometer) for these purposes. The animals were then administered the test compounds at 10, 5.0 and 1.0 mg./kg., respectively, or the control vehicle alone, via the intravenous route of administration, at 90 minutes following the start of the pentagastrin infusion. Gastric antisecretory effects were thereafter calculated by comparing the lowest acid output after drug administration with the mean acid output immediately prior to same and the results obtained in this manner are reported in the following table, where the entries given for each individual compound are expressed in terms of percent inhibition (%) at the dose level indicated:

| Pyridylaminotriazole | Acid Antisecretory Activity (% Inhibition) | | |
|---|---|---|---|
| | 1.0 mg./kg. | 5.0 mg./kg. | 10 mg./kg. |
| Product of Example I | 33 | 64 | — |
| Product of Example II | 0 | — | 40 |
| Product of Example III | — | — | 14 |
| Product of Example IV | 31 | — | — |
| Product of Example V | 23 | — | 34 |
| Product of Example VII | 11 | — | — |
| Product of Example VIII | 48 | 80 | 96 |
| Product of Example IX | 53 | — | — |
| Product of Example X | — | 68 | — |
| Product of Example XI | 38 | — | — |
| Product of Example XII | 18 | — | 50 |
| Product of Example XIV | 21 | — | 72 |
| Product of Example XV | 21 | — | 62 |
| Product of Example XVI | — | 33 | — |
| Product of Example XVIII | 30 | 86 | 94 |
| Product of Example XIX | 50 | — | — |
| Product of Example XX | 51 | 89 | 93 |
| Product of Example XXII | 29 | — | — |
| Product of Example XXIII | 35 | 52 | — |
| Product of Example XXV | 10 | — | — |
| Product of Example XXVI | 32 | 64 | — |
| Product of Example XXVIII | — | 49 | — |
| Product of Example XXXII | — | — | 25 |

I claim:

1. A compound selected from the group consisting of 3-amino-5-(4-pyridyl)-1,2,4-triazole bases of the formula:

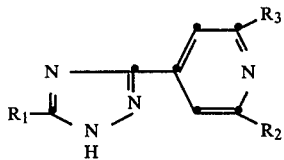

and the pharmaceutically acceptable acid addition salts thereof, wherein $R_1$ is a member selected from the group consisting of amino, lower N-monoalkylamino and lower N,N-dialkylamino;

$R_2$ is a member selected from the group consisting of amino, N-monoalkylamino having from one to twelve carbon atoms, N,N-dialkylamino wherein at least one of said alkyl moieties is either methyl or ethyl and the other is alkyl having from one to twelve carbon atoms, N-monoallylamino, N-monomethallylamino, N-methyl-N-allylamino, N-ethyl-N-allylamino, N-mono($\beta$-hydroxyethyl)amino, N-mono($\gamma$-hydroxypropyl)amino, N-mono[$\beta$-(lower alkoxy)ethyl]amino, N-mono[$\gamma$-(lower alkoxy)propyl]amino, N-mono(2,2,2-trifluoroethyl)amino, N-monobenzylamino, N-methyl-N-benzylamino, N-ethyl-N-benzylamino, N-mono($\beta$-phenylethyl)amino, N-mono($\beta$-phenyl-$\beta$-hydroxyethyl)amino, and ring-substituted N-monobenzylamino, ring-substituted N-methyl-N-benzylamino, ring-substituted N-ethyl-N-benzylamino and ring-substituted N-mono($\beta$-phenylethyl)amino with each ring having up to two substituents on the phenyl moiety wherein each of said ring-substituents is identically chosen from the group consisting of fluorine, chlorine, bromine, trifluoromethyl, lower alkyl, lower alkoxy, hydroxy, carbamoyl, sulfamoyl, lower alkylsulfonyl and methanesulfonamido, or is separately chosen from the group consisting of chlorine, methyl, methoxy, hydroxy and trifluoromethyl; and $R_3$ is a member selected from the group consisting of hydrogen, lower alkyl, amino and lower-N-monoalkylamino.

2. A compound as claimed in claim 1 wherein $R_1$ and $R_2$ are each amino and $R_3$ is hydrogen.

3. A hydrogen as claimed in claim 1 wherein $R_1$ is amino, $R_2$ is N-monoalkylamino having from one to twelve carbon atoms and $R_3$ is hydrogen.

4. A compound as claimed in claim 1 wherein $R_1$ is lower N-monoalkylamino, $R_2$ is N-monoalkylamino having from one to twelve carbon atoms and $R_3$ is hydrogen.

5. A compound as claimed in claim 1 wherein $R_1$ is amino, $R_2$ is N,N-dialkylamino wherein at least one of said alkyl moieties is either methyl or ethyl and the other is alkyl having from one to twelve carbon atoms, and $R_3$ is hydrogen.

6. A compound as claimed in claim 1 wherein $R_1$ is amino, $R_2$ is N-monoallylamino and $R_3$ is hydrogen.

7. A compound as claimed in claim 1 wherein $R_1$ is amino, $R_2$ is N-mono-($\beta$-hydroxyethyl)amino and $R_3$ is hydrogen.

8. A compound as claimed in claim 1 wherein $R_1$ is amino, $R_2$ is N-monobenzylamino and $R_3$ is hydrogen.

9. A compound as claimed in claim 1 wherein $R_1$ is amino, $R_2$ is N-mono($\beta$-phenylethyl)amino and $R_3$ is hydrogen.

10. A compound as claimed in claim 1 wherein $R_1$ is amino, $R_2$ is N-mono(p-chlorobenzyl)amino and $R_3$ is hydrogen.

11. A compound as claimed in claim 1 wherein $R_1$ and $R_2$ are each amino and $R_3$ is lower alkyl.

12. A compound as claimed in claim 1 wherein $R_1$, $R_2$ and $R_3$ are each amino.

13. A compound as claimed in claim 3 wherein $R_2$ is N-monomethylamino.

14. A compound as claimed in claim 3 wherein $R_2$ is N-monoethylamino.

15. A compound as claimed in claim 3 wherein $R_2$ is N-monopropylamino.

16. A compound as claimed in claim 4 wherein $R_1$ is N-monomethylamino and $R_2$ is N-monoethylamino.

17. A compound as claimed in claim 4 wherein $R_1$ and $R_2$ are each N-monoethylamino.

18. A compound as claimed in claim 5 wherein $R_2$ is N,N-dimethylamino.

19. A compound as claimed in claim 5 wherein $R_2$ is N-ethyl-N-methylamino.

20. A compound as claimed in claim 5 wherein $R_2$ is N,N-diethylamino.

21. 3-Amino-5-[2-(N-monomethylamino)-4-pyridyl]-1,2,4-triazole.

22. 3-Amino-5-[2-(N-monoethylamino)-4-pyridyl]-1,2,4-trizole.

23. 3-Amino-5-[2-(N,N-dimethylamino)-4-pyridyl]-1,2,4-triazole.

24. A method for combatting peptic ulcers in the treatment of a subject afflicted with said condition, which comprises administering to said subject a anti-ulcer effective amount of a compound as claimed in claim 1.

25. A pharmaceutical composition suitable for oral administration comprising a pharmaceutically acceptable carrier and a anti-ulcer effective amount of an anti-ulcer agent wherein said agent is a compound as claimed in claim 1.

* * * * *